April 20, 1948. G. E. BANTEL Plant Pat. 796
SANSEVIERIA PLANT
Filed July 24, 1946
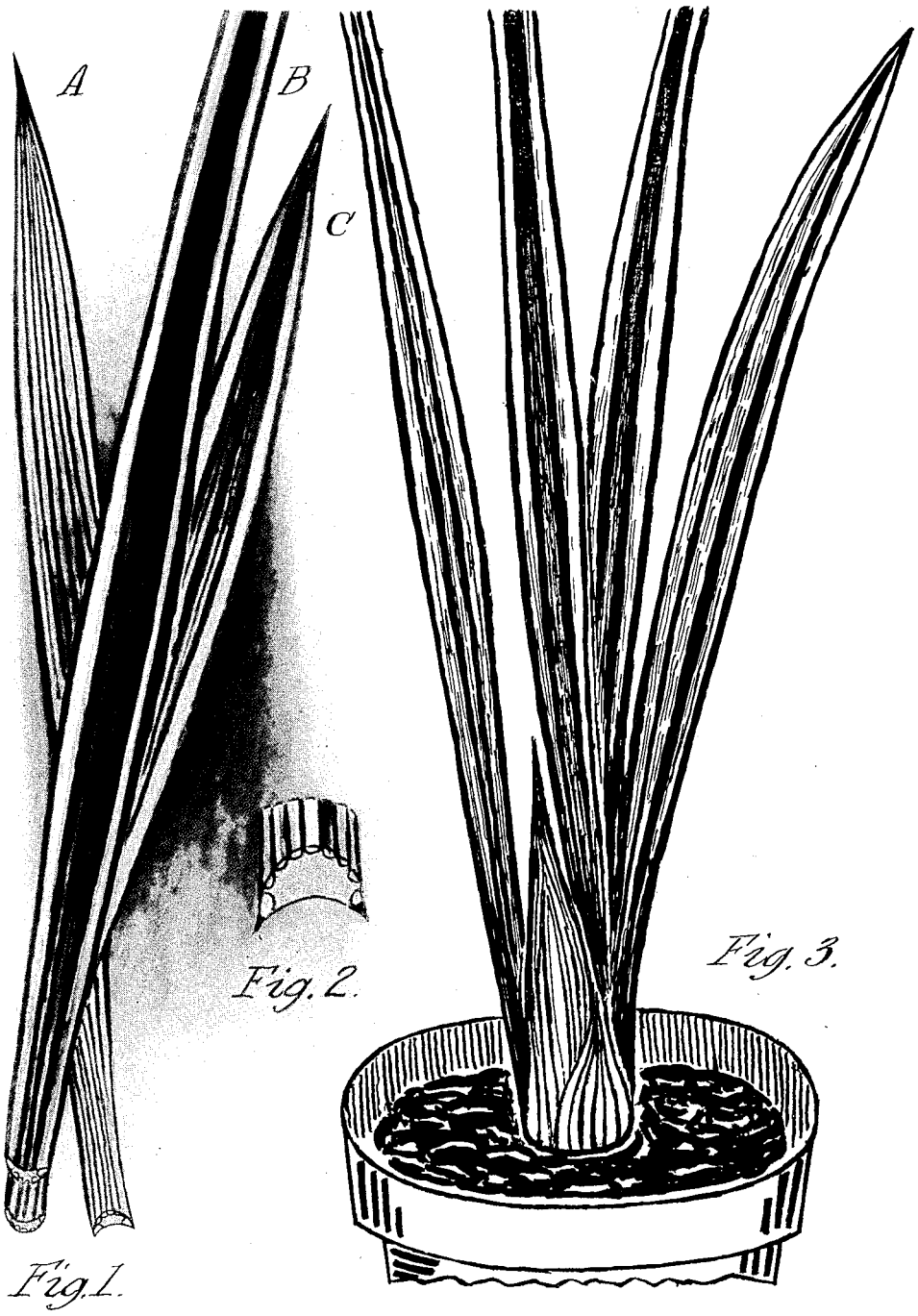
WITNESS
Addison J. Avery
INVENTOR
GUSTAV E BANTEL
Rummler & Rummler & Davis,
ATTYS.

Patented Apr. 20, 1948

Plant Pat. 796

UNITED STATES PATENT OFFICE

796

SANSEVIERIA PLANT

Gustav E. Bantel, St. Louis, Mo., assignor to
Frank L. Sieloff, St. Louis, Mo.

Application July 24, 1946, Serial No. 685,978

1 Claim. (Cl. 47—59)

My present discovery relates to a new and improved variety of sansevieria plant, the principal claim to novelty residing in the form and coloring of its linear ensiform, channeled leaves.

This new variety is a sport of the variety *S. laurentii* and has been asexually reproduced by division and from rhizomes, and its characteristics have become permanently fixed.

The primary object in carrying out this invention was to fix the unusual dark olive green and silver-white longitudinal stripes of the leaves, their slender transversely concave rapier shape, and their nearly vertical stiff erectness, diverging upwardly from a short basal rosette.

This new variety in plant structure is similar to the ordinary sansevieria in that its erect leaves spring from a basal rosette, two to four or more to a single plant with two to five additional much smaller oblong-lanceolate sheath-like leaves tightly clasping the base. However, it differs distinctly in having its slender ensiform leaves stiffly erect, deeply channeled in the lower portion, extending to 24 inches or more in height with their greatest width about 1¼ inches well above the middle and then gradually tapering in graceful curvature to an acute stiff point. In color the inner concave face of the leaf is mostly dark olive green longitudinally streaked with silver-white. Each leaf, on its inner face, is outlined by a narrow marginal streak of dark green inward of which is a narrow streak of silver-white and the intermediate portion of the leaf surface is dark green with faint longitudinal streaks of gray.

The outer convexly curved face is much lighter in color in that the dark green streaks are narrower and more numerous and are interspersed with narrow streaks of silver-white, the white being wider and predominating. In section the lower portion of the leaf is crescent shape, being fleshy in its middle part and tapering outwardly to a thin edge. In some plants the light streaks are of pale yellowish color instead of silver and the green streaks are of pleasantly lighter or dark dull yellow-green, but are otherwise characteristically the same.

The accompanying illustrations show:

Figure 1 illustrates the leaves in approximately their true colors.

Fig. 2 shows a transverse section of a leaf, taken in the lower part of its length.

Fig. 3 shows in black and white the general form of the plant.

Unlike the ordinary sansevieria, which has the bands of greenish white zig-zagging across the leaves, this new variety has silver-colored longitudinal strips running from its base to the tip of each leaf, and the plant spreads very little from the base to the tip. The leaves are approximately 24 inches in length and about 1 inch in width. They are comparatively thick down the middle, tapering to thin edges, thus giving them a channel-like or wedge-shaped appearance. The well-known sansevieria has a flatter leaf averaging about the same thickness throughout, and rippling at the outer edges.

In Fig. 1, the leaf A shows the color distribution on the outer convex side of the leaf, the leaf B shows the coloring of the inner concave side of the leaf, and the leaf C shows the variation in which the light streaks tend toward a pale yellow and the dark streaks are of a lighter olive green.

The color designations according to "A Dictionary of Color," by Maerz and Paul, are as follows:

| Figure | Item | Plate | Letter | No. |
|---|---|---|---|---|
| 1-A | Main leaf face color a dark-black green. | 24 | C | 7 |
| | Shading into | 30 | A | 5 |
| | Streaked | 17 | A | 2 |
| 1-B | Back of leaf more pronouncedly striped with— | 17 | A | 2 |
| 1-C | Main leaf face | 9 | H | 1 |
| | Shading into | 11 | D | 1 |
| | Streaked with dark olive green | 31 | A | 8 |
| 2 | Center area of cross section of base of 1 leaf shows cog-like structure of pale green surrounded by white tissue corresponding to light streaks on leaf, while darker sections of leaf radiate from pale green center area. | 18 | G | 5 |

This new variety of sansevieria is easily distinguished from other known varieties by its unusual longitudinal stripes, its stiff rapier-shaped leaves, and its compact growth with little tendency of the leaves to spread or bend.

Having thus disclosed my discovery, I claim:

A new and distinct variety of sansevieria plant, substantially as shown and described, characterized particularly by its stiffly erect ensiform leaves, marked with alternating longitudinal stripes of white and green.

GUSTAV E. BANTEL.